(12) United States Patent
Kalkbrenner et al.

(10) Patent No.: US 10,539,505 B2
(45) Date of Patent: Jan. 21, 2020

(54) METHOD FOR CREATING A DIGITAL FLUORESCENT IMAGE

(71) Applicant: Carl Zeiss Microscopy GmbH, Jena (DE)

(72) Inventors: Thomas Kalkbrenner, Jena (DE); Ralf Wolleschensky, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 15/746,732

(22) PCT Filed: Jul. 27, 2016

(86) PCT No.: PCT/DE2016/100341
§ 371 (c)(1),
(2) Date: Jan. 22, 2018

(87) PCT Pub. No.: WO2017/020887
PCT Pub. Date: Feb. 9, 2017

(65) Prior Publication Data
US 2019/0003967 A1      Jan. 3, 2019

(30) Foreign Application Priority Data
Jul. 31, 2015   (DE) .......... 10 2015 112 628

(51) Int. Cl.
*G01N 21/64*   (2006.01)
*G02B 21/00*   (2006.01)
*G02B 27/58*   (2006.01)
*G06T 3/40*    (2006.01)

(52) U.S. Cl.
CPC ..... *G01N 21/6408* (2013.01); *G01N 21/6458* (2013.01); *G02B 21/008* (2013.01); *G02B 21/0076* (2013.01); *G02B 27/58* (2013.01); *G06T 3/4053* (2013.01)

(58) Field of Classification Search
CPC .. G01N 21/6458; G02B 27/58; G02B 21/367; G02B 21/0076; G06T 3/4053
See application file for complete search history.

(56) References Cited

U.S. PATENT DOCUMENTS

| | | |
|---|---|---|
| 2004/0257646 A1 | 12/2004 | Wachsmuth |
| 2006/0146325 A1 | 7/2006 | Wachsmuth et al. |
| 2007/0103687 A1 | 5/2007 | Okazaki |
| 2007/0197894 A1* | 8/2007 | Jo ................ A61B 5/0059 |
| | | 600/407 |
| 2007/0257182 A1 | 11/2007 | Sawada et al. |

(Continued)

FOREIGN PATENT DOCUMENTS

| | | |
|---|---|---|
| DE | 10 2005 000 915 A1 | 7/2006 |
| DE | 10 2011 077 269 A1 | 12/2012 |

(Continued)

*Primary Examiner* — Kenneth J Malkowski
(74) *Attorney, Agent, or Firm* — Duane Morris LLP

(57) ABSTRACT

In a method for creating a digital fluorescent image, the light emitted per pixel from an object plane is converted into a sequence of amplitudes, each of which is associated with one specific measurement time, the sequence of amplitudes is auto-correlated in a manner that is delayed by at least one time offset, and a specific correlation amplitude, from which a total amplitude is determined, is formed for each of the time offsets.

13 Claims, 1 Drawing Sheet

(56) References Cited

U.S. PATENT DOCUMENTS

| | | |
|---|---|---|
| 2010/0303386 A1 | 12/2010 | Enderlein |
| 2011/0119034 A1 | 5/2011 | Liedtke et al. |
| 2011/0317910 A1 | 12/2011 | Suzuki |
| 2014/0184777 A1 | 7/2014 | Kleppe et al. |
| 2015/0035964 A1 | 2/2015 | Kleppe et al. |
| 2018/0113292 A1* | 4/2018 | Novikau .............. G02B 21/006 |

FOREIGN PATENT DOCUMENTS

| | | |
|---|---|---|
| DE | 10 2011 084 315 A1 | 4/2013 |
| EP | 1 524 541 A1 | 4/2005 |
| EP | 2 533 048 A1 | 12/2012 |
| WO | WO 03/050535 A2 | 6/2003 |
| WO | WO 2009/034458 A2 | 3/2009 |

\* cited by examiner

METHOD FOR CREATING A DIGITAL FLUORESCENT IMAGE

RELATED APPLICATIONS

The present application is a U.S. National Stage application of International PCT Application No. PCT/DE2016/100341 filed on Jul. 27, 2016 which claims priority benefit of German Application No. DE 10 2015 112 628.1 filed on Jul. 31, 2015, the contents of each are incorporated by reference in their entirety.

FIELD OF THE INVENTION

The invention relates to a method by which a digital fluorescent image (electronic image file) of a sample provided with a fluorescent dye is created.

BACKGROUND OF THE INVENTION

Fluorescence microscopy is a very effective light microscopy method for locating proteins and for imaging protein distributions in tissue samples and cells (hereinafter called sample). For this purpose, the sample to be microscoped is selectively supplied with fluorescent dyes which dock to the proteins. By illumination with light (excitation light) of a specific wavelength (excitation wavelength), depending on the dye used, the latter is excited and electrons of the dye molecules (fluorophores) are raised to a higher energy level. After a short dwell time, the excited electrons return to their original level, each emitting light (emission light) of a specific wavelength (emission wavelength), which is longer than the excitation wavelength. In this case, a single electron emits a light quantum or photon. This property is used to visualize proteins or other substances.

Fluorescence microscopes, unless they serve exclusively for visual examination of the sample, are divided into classic wide-field microscopes, with a camera comprising a plurality of detectors arranged in a matrix, and into laser-scanning microscopes comprising only one single detector. Both types of microscopes are common nowadays, with the laser-scanning microscopes having many advantages over the classic wide-field fluorescence microscopes.

Laser-scanning microscopes are usually confocal microscopes, which means the focus of the excitation light, which is placed in the object plane, is imaged into a conjugated plane, i.e. the image plane, where a single detector is positioned, usually with a pinhole in front of it. In this manner, only emission light of a tiny object field portion, i.e. of a tiny pixel, is directed onto the detector. This has the decisive advantage over the classic wide-field fluorescence microscope that only light quantums of the emission light coming from the focal plane are detected and contribute to signal formation. In this manner, samples can be microscoped layer by layer, and the fluorescent images generated from the signals for each microscoped layer can be combined into a three-dimensional image.

The fluorescent images per layer are obtained by the object field being scanned by a laser scanning system, usually consisting of two galvanometric mirrors, at a scanning frequency resulting in a pixel dwell time per pixel. The emission light received by the detector during the pixel dwell time is converted by the detector into electrical analog detector signals which, in knowledge of the respective position of the laser scanning system, are each associated with a respective pixel. At first, the analog detector signals are digitized at a predetermined clock frequency. For this purpose, two types of digitization are basically known in the field of laser scanning microscopy.

A first type of digitization is the integration via the analog detector signal. It is used when the duration of the signal detection (detection time) is of the same magnitude as the pixel dwell time, i.e. the detection time is only marginally shorter than the pixel dwell time. Based on the integral value formed via the analog signal in this case and the detection time, one mean value per pixel (mean amplitude) can be derived from one single readout of the detector, representing a total amplitude associated with the pixel.

In the past, due to the low radiation intensity of the fluorescent dyes, particular use was made of this integration method, because it allows a comparatively high total amplitude to be formed.

A second type of digitization is the fast sampling of the analog detector signal. It is preferably used if the detection time is considerably shorter, in particular several orders of magnitude shorter than the pixel dwell time. Via the pixel dwell time, a respective amplitude is generated for each of a plurality of measuring times (the duration of signal detection being simply regarded as a point in time, or the measuring time being the time at which the detector is read out) and a mean value (mean amplitude) is formed from the sequence of amplitudes and assigned as the total amplitude to one respective pixel.

Today, this fast sampling is common in laser scanning microscopy because, when using modern A/D converters, the advantages of the method prevail.

Typically, the detector signal is converted at a constant sampling rate which is considerably, preferably at least one order of magnitude, in particular two orders of magnitude, higher than the shortest possible pixel dwell time. The number of measuring times per pixel is then obtained from the pixel dwell time. The latter is in turn defined by the scanning setting (frame rate, pixel number, scan size). An increase in pixel dwell time then results in an increase in the number of measuring times per pixel.

In order to improve the signal-to-noise ratio, the pixel dwell time is usually increased. This has the disadvantage of increasing the total time for obtaining a fluorescent image formed from the total amplitudes for all pixels in the form of raster graphics and of decreasing the frame rate. The signal-to-noise ratio is determined by the ratio of the amounts of the total amplitude which are caused, on the one hand, by the emission light and, on the other hand, by the noise.

OBJECT OF THE INVENTION

It is the object of the invention to find a method which provides a digital fluorescent image with an improved signal-to-noise ratio while maintaining the frame rate.

The object is achieved by a method for creating a digital fluorescent image, wherein a sample provided with a fluorescent dye is arranged in an object plane of a laser-scanning microscope and is acted upon by excitation light in a time sequence, pixel-by-pixel over a pixel dwell time, whereby an emission light is generated per pixel. The emission light per pixel is detected by a detector and converted into a sequence of amplitudes, each associated with one respective measuring time. From these amplitudes, one respective total amplitude per pixel is formed. The total amplitudes of all pixels are combined into a fluorescent image. It is essential to the invention that the total amplitude associated with a respective pixel be obtained from one or more correlation amplitudes, thereby virtually preventing inclusion of the noise in the total amplitude, so that a fluorescent image with a higher signal-to-noise ratio results.

For this purpose, the sequence of amplitudes beginning at a later measuring time is correlated at least once with the same sequence of amplitudes beginning at an earlier measuring time. There is a time lag between the later measuring times and the earlier measuring times. This means that, instead of only one autocorrelation with a time lag, the sequence of amplitudes may be autocorrelated several times, applying a different time lag to each autocorrelation. For each time lag, a correlation amplitude specific to the respective time lag is formed and the total amplitude is obtained from the correlation amplitudes formed. The number of correlatable amplitude pairs corresponds to the number of all measuring times per pixel dwell time minus the time lag.

The correlation amplitude is preferably calculated using the formula:

$$K_\tau = ((I(t_n) - I_{mean}) \times (I(t_m) - I_{mean}))_{mean}$$

wherein $I(t_n)$ represents the amplitudes (I) of the earlier measuring times $(t_n)$, $I(t_m)$ represents the amplitudes (I) of the later measuring times $(t_m)$, $m=n+\tau$, and $I_{mean}$ is a mean amplitude computed by averaging all amplitudes.

Advantageously, the correlation amplitude $K_\tau$ is standardized by dividing it by the root mean square amplitude $I_{mean}^2$.

The quality of the fluorescent image can be improved if the correlation amplitude $K_\tau$ is calculated for different time lags $\tau$ and the time lag $\tau$ having the comparatively largest correlation amplitude $K_\tau$ is determined and used as the total amplitude.

The time lag $\tau$ associated with the comparatively greatest correlation amplitude $K_\tau$ may advantageously be stored, associated with the fluorescent dye, in a database.

Alternatively, the correlation amplitude $K_\tau$ can be calculated for different time lags $\tau$ and the mean value of the correlation amplitudes $K_\tau$ can be determined and used as the total amplitude.

Also, the correlation amplitude $K_\tau$ can be calculated for different time lags $\tau$ and the sum of the correlation amplitudes $K_\tau$ is determined and used as the total amplitude.

Advantageously, the number of measuring times is greater than 400 and the time lag $\tau$ is between 50 and 150, so that at least 250 amplitude pairs are correlated.

The method of the invention makes use of the fact that the fluorescent dyes are subject to at least one correlating process when emitting emission light, which means that the fluorescent signal which represents the intensity of the emission light for the duration of the pixel dwell time, is subject to at least one function.

Known correlating processes in this case are e.g. photoblinking and photobleaching.

Photoblinking refers to the emission of photons for a specific period in alternation with a dark state. An electron of a fluorescent substance irradiated with excitation light is raised to a higher energy level and gives off a photon as it returns to the lower energy level. However, this does not happen continuously, but there are phases in-between, known as the dark state, in which no photons are emitted. This dark state may be, for example, a so-called triplet state or any other state out of which no fluorescent emission can take place. When observing the fluorophores, keeping the detection time so small that only one photon impinges on the receiver within the detection time ensures that a typical on/off phenomenon will result. The time scales of this phenomenon and its exact causes are diverse and not known to the last detail. Assuming that the fluorophores behave statically, i.e. their number within a pixel remains unchanged at least over the pixel dwell time, cyclic intensity variations can be detected due to the blinking in the case of a short dwell time.

Photobleaching refers to the irreversible transition of a fluorophore to a non-fluorescent state. The time scales of this phenomenon and its causes are also diverse and not known to the last detail. What is known is the dependence of photobleaching on the intensity of the excitation light. Especially with the typically strong focusing of excitation light into the sample in the case of a confocal laser scanning microscope, photobleaching is a very fast-progressing process. In general, photobleaching is an undesired process in fluorescence microscopy, since it causes the fluorescence signal to decrease with progressing duration of observation.

It is also known that both phenomena (photobleaching and photoblinking) have different manifestations for different fluorescent substances and in different ambient conditions (temperature, pH value, oxygen concentration).

Both photoblinking and photobleaching lead to a deteriorated total signal, since less emission light formed by the sum of photons is detected and the signal-to-noise ratio consequently deteriorates.

Carrying out the method of the invention does not require knowledge of the time scales and the sequence of the aforementioned processes or, as the case may be, other correlating processes taking place, but merely knowledge of the fact that they happen and are used for signal processing.

The correlating processes are used for signal processing in that a total amplitude for a respective pixel is not formed according to the prior art, e.g. by averaging a sequence of amplitudes, but by autocorrelation of the sequence of amplitudes.

Autocorrelation is basically known from signal processing and describes the correlation of a signal (function) or of a sequence of amplitudes with itself at an earlier point in time.

The application of the autocorrelation method is also known from fluorescence correlation spectroscopy, wherein information is obtained from the change in intensity of the emission light as a function over time. A correlation function is formed via a time lag of the function correlating with itself. Based on the correlation function thus formed, the diffusion time may be derived, for example, which corresponds to the time it takes the correlation amplitude to decrease from a maximum to a specific level, e.g. half its level, within only a minimal time lag between the correlating functions.

BRIEF DESCRIPTION OF THE DRAWINGS

The method according to the invention will be explained in more detail below with reference to an exemplary embodiment and to the Figures, wherein.

DESCRIPTION OF THE EMBODIMENTS

Up to the point of obtaining amplitudes associated with the individual measuring times within a pixel dwell time, a method according to the invention is the same as the method described in the prior art with digitization of an analog detector signal by fast sampling.

It is essential for the analog detector signal to be digitized by multiple sampling (readout of the detector) into a sequence of a large number of amplitudes. In practice, this is only possible with individual detectors and, therefore, with a laser scanning microscope, which may be typically embodied as a single-spot arrangement, but may also be embodied as a multi-spot arrangement, wherein e.g. four separate beams are simultaneously scanned over the sample so that fluorescent radiation is detected by four associated individual detectors. Instead of being acted upon by excitation light pixel by pixel, an object field may principally also be illuminated simultaneously, while a detector arrangement of a camera may be read out several times. In practice, however, the short detection times in the μs range required for detection of photoblinking are not achieved with typical cameras. Moreover, the radiation intensities that would respectively impinge on a pixel and the number of potential measuring times are too low to obtain a sufficient number of sufficiently high amplitudes for autocorrelation.

In order to generate a fluorescent image, excitation light coming from an excitation light source is sequentially focussed into an object plane, which is located in or on a sample marked with a fluorescent dye, into individual object field sections (pixels) by means of a scanning system sequentially, for a respective pixel dwell time T in each instance. This excites the fluorophores in each respective pixel to emit emission light. The intensity of the emission light coming from a pixel during the pixel dwell time T, determined by the number of photons emitted, is detected by a detector.

Figure 1:
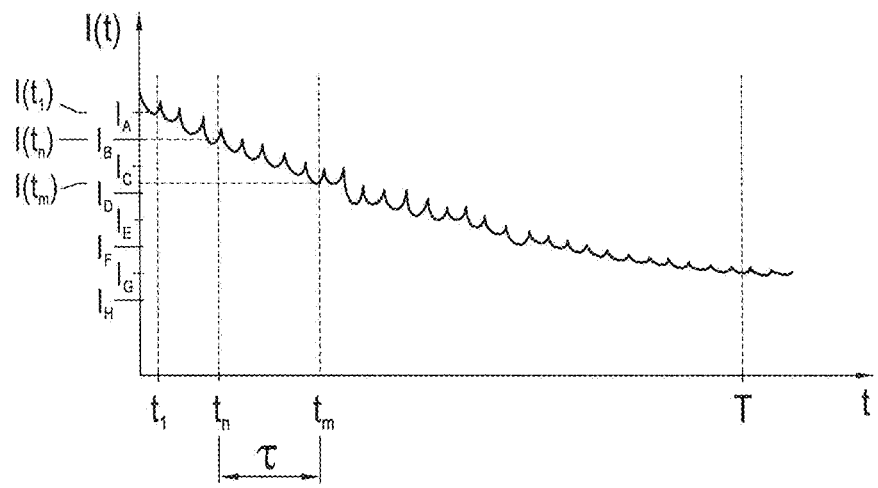
FIG. 1 shows the radiation intensity (amplitude) I(t) of the fluorescence light as a function of the time t for a pixel dwell time T.

FIG. 1 shows the analog signal of the radiation intensity I(t) of the fluorescence light as a function of the time t for the pixel dwell time T. It is subject to a function caused by photobleaching and similar to a descending exponential function, and to a function fluctuating on a shorter time scale and caused by photoblinking.

In an A/D conversion process, the detector is read out at several measuring times whose distance from each other is determined by the detection time and one amplitude is formed for each measuring time. The analog signal of the intensity of the emission light during the pixel dwell time T is thus converted into a digital signal, with a sequence of amplitudes which are proportional to the intensities respectively detected during a detection time and are associated with a measuring time. The shorter the detection time with respect to the pixel dwell time T, the higher the sampling frequency and, thus, the resolution of the analog function.

The intensity associated with a measuring time is formed by the sum of the impinging photons as well as the usual noise contributions in the detection time associated with the respective measuring time.

Thus, after a pixel dwell time T a plurality of amplitudes is present for a pixel, which form a sequence by being each associated with a respective measuring time. In contrast to the prior art, where a total amplitude is formed from the average of all amplitudes as a mean amplitude, a method according to the invention provides for autocorrelation of the sequence of amplitudes with itself, delayed by a time lag $\tau$, to form a correlation amplitude $K_\tau$. In this case, the time lag $\tau$ is to be understood as the dimensionless number of measuring points between the amplitudes of the sequence to be autocorrelated. This means that the sequence of amplitudes beginning at the first measuring time $t_1$ and beginning at the twentieth measuring time $t_{20}$ is to be correlated, in which case the time lag $\tau$ equals 19. The actual duration of the time lag $\tau$ results from the detection time and the time lag $\tau$.

The amplitudes, forming respective amplitude pairs, of earlier measuring times $t_n$ and later measuring times $t_m$ with a fixed time lag $\tau$, so that m=n+$\tau$, are continuously correlated with each other. For the sake of clarity, the amplitude is referred to as I(t) even after conversion of the optical signal into an electrical signal. The correlation amplitude $K_\tau$ for a respective time lag $\tau$ results from the correlation of the earlier amplitudes I($t_n$) and the later amplitudes I($t_m$), whose measuring times have the time lag $\tau$ with respect to each other, and from the average of the amplitudes $I_{mean}$ according to the following formula:

$$K_\tau=((I(t_n)-I_{mean})\times(I(t_m)-I_{mean}))_{mean}$$

Advantageously, the correlation amplitude $K_\tau$ can be standardized, for example with the root mean square of the amplitudes (mean amplitude), which results in the following formula:

$$K_\tau=((I(t_n)-I_{mean})\times(I(t_m)-I_{mean}))_{mean}$$

or with the root square maximum value of the amplitudes, which results in the following formula:

$$K_\tau=((I(t_n)-I_{mean})\times(I(t_m)-I_{mean}))_{mean}$$

At any later measuring time $t_m$, a product will be formed from the difference between the amplitude I($t_n$) at the associated earlier measuring time $t_n$ and the average of all amplitudes $I_{mean}$ and the difference between the amplitude I($t_{n+\tau}$) at the respective later measuring time $t_{n+\tau}$ and the average of all amplitudes $I_{mean}$. This results in a sequence of product values, which are associated with the later measuring times $t_m$ and whose average represents the correlation amplitude $K_\tau$. The correlation amplitude $K_\tau$ thus obtained is free from noise, due to not being subject to any correlation.

For example, a 256×256 pixel scan at 1 frame/s, with a pixel dwell time of T=15 μs and a sampling frequency of 40 MHz, results in 610 measuring times. Thus, 610 amplitudes I($t_n$) of so-called earlier measuring times $t_n$ are available, wherein 1≤n≤610.

In order to provide a high number of amplitudes I($t_{n+\tau}$) of so-called later measuring times $t_m$ for autocorrelation in order to determine the correlation amplitude $K_\tau$, the duration of the time lag $\tau$ should preferably be less than half the pixel dwell time T, but also greater than a fifth of the pixel dwell time T. Accordingly, in the present example, the time lag $\tau$ could advantageously correspond to the number of measuring times between the first measuring time $t_1$ and the one hundred and twentieth measuring time $t_{120}$, so that the time lag τ would equal 119. In this case, 410 amplitude pairs would be correlated.

Basically, the time lag τ can also be very small, however, up to approx. 10, based on the exemplary embodiment, or very large, up to approx. 550.

Digital fluorescent images are usually represented and stored as raster graphics, which means that the amplitudes associated with the pixels are stored in a raster correlating with the arrangement of the pixels in the object plane.

In order to generate fluorescent images which are to be created for samples provided with different fluorescent substances, it makes sense to experimentally determine a respective optimal time lag τ for which the resulting correlation amplitude $K_τ$ is maximal and to store the duration of the optimal time lag τ in a database.

For this purpose, short local measurements can be automatically performed on individual pixels, in particular in a region of the object plane in which high fluorescence signals are expected, and the amplitudes obtained thereby can be computed as described above for different time lags τ. These local measurements may be automatically distributed stochastically or equidistantly over the object region. However, the locations of the local measurements may also be defined by the user in order to analyze particularly relevant sample regions.

The duration of the optimal time lag τ may also be obtained from a database. Characteristic photoblinking times are known from the literature for many typical dyes and constitute the optimal duration of a time lag τ. These literature values can be stored, in a manner associated with a fluorescent substance, in the database, thus allowing at least an initial time lag to be derived for microscoping later samples with an identical fluorescent substance, in knowledge of the detection time.

Prior art averaging usually takes place on an FPGA (Field Programmable Gate Array). Forming the autocorrelation amplitudes may also be implemented on an FPGA.

Also, the same digital detector signal, formed by the amplitudes 1 respectively associated with the measuring times during a pixel dwell time T, may be used to determine the total amplitudes in parallel or one after another by averaging and autocorrelation and represented as a fluorescent image.

As explained, the correlation amplitude $K_τ$ for a pixel may be determined for different time lags τ and one of them may be used to represent the fluorescent image. Also, for each pixel, several correlation amplitudes $K_τ$ computed for different time lags τ may be added up and/or averaged for representation of the fluorescent image. Thus, the signal-to-noise ratio can be further improved, in particular if the optimal duration of the time lag τ is not known a priori.

Figure 2A:
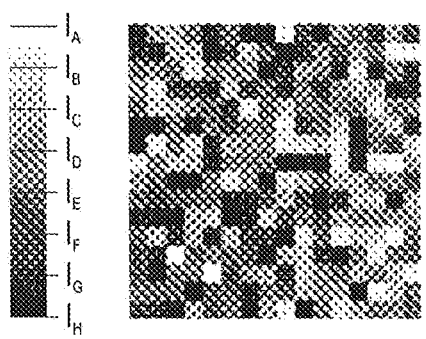
FIG. 2a shows a visualized digital fluorescent image, wherein the total amplitudes determining the grayscale value of the image pixels were obtained by averaging according to the prior art (different grayscale values being represented here by different types of hatching)
Figure 2B:
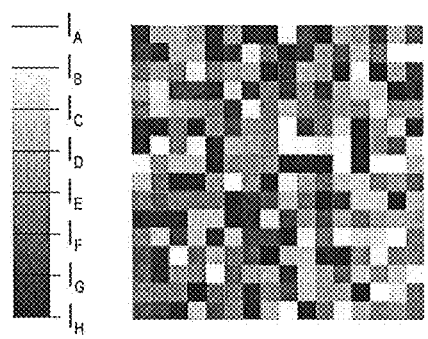
FIG. 2b shows a visualized digital fluorescent image, wherein the total amplitudes determining the grayscale value of the image pixels were obtained by averaging according to the prior art (different grayscale values being represented here by different types of hatching)

FIGS. 2a and 2b each show a respective fluorescent image created according to the prior art by association of one mean amplitude per pixel. The figures differ in that differently high mean amplitudes are represented, on the one hand, by different types of hatching and, on the other hand, by different grayscale values.

Figure 3A:
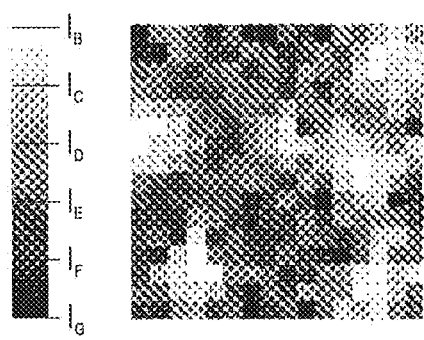
FIG. 3a shows a visualized digital fluorescent image, wherein the total amplitudes determining the grayscale value of the image pixels were obtained by autocorrelation according to the invention (different grayscale values being represented here by different types of hatching)
Figure 3B:
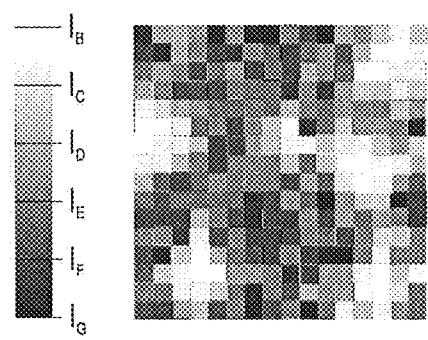
FIG. 3b shows a visualized digital fluorescent image, wherein the total amplitudes determining the grayscale value of the image pixels were obtained by autocorrelation according to the invention (different grayscale values being represented here by different grayscale levels).

FIGS. 3a and 3b each show a respective fluorescent image created according to the invention by association of one correlation amplitude $K_τ$ per pixel. The figures differ in that differently high mean amplitudes are represented, on the one hand, by different types of hatching and, on the other hand, by different grayscale values.

FIGS. 3a and 3b show what is called clustering, indicating a local concentration of the fluorescent substances in the object plane. Such clustering is not evident in FIGS. 2a and 2b due to the overlap of the fluorescence signal and the noise.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A method for creating a digital fluorescent image, comprising:

arranging a sample with a fluorescent substance in an object plane of a laser-scanning microscope;

having excitation light act upon said sample in a time sequence, pixel-by-pixel over a pixel dwell time, so that emission light is generated per pixel which is detected by a detector and converted into a sequence of amplitudes, which are each associated with a respective measuring time and from which a total amplitude is formed;

combining the total amplitudes of all pixels into exactly one fluorescent image; and autocorrelating the sequence of amplitudes for each pixel, beginning at a later measuring time is autocorrelated at least once with the same sequence of amplitudes beginning at an earlier measuring time which has a time lag with respect to the later measuring time, for the time lag at least one respective specific correlation amplitude is formed and the total amplitude is determined from the at least one correlation amplitude formed.

2. The method according to claim 1, wherein a correlation amplitude is calculated using the formula:

$$K_τ=((I(t_n)-I_{mean})×(I(t_m)-I_{mean}))_{mean}$$

wherein $I(t_n)$ represents the amplitudes of the earlier measuring times, $I(t_m)$ represents the amplitudes of the later measuring times, m=n+τ, and $I_{mean}$ is a mean value of the amplitudes.

3. The method according to claim 2, wherein the correlation amplitude is standardized by dividing it by the root mean square of the amplitudes.

4. The method according to claim 1, wherein the correlation amplitude is calculated for different time lags and the time lag having the comparatively largest correlation amplitude is determined and used as the total amplitude.

5. The method according to claim 4, wherein the time lag with the comparatively largest total amplitude is associated with the fluorescent dye and stored in a database.

6. The method according to claim 1, wherein the correlation amplitude is calculated for different time lags and the mean value of the correlation amplitudes is determined and used as the total amplitude.

7. The method according to claim 1, wherein the correlation amplitude is calculated for different time lags and the sum of the correlation amplitudes is determined and used as the total amplitude.

8. The method according to claim 6, wherein the number of measuring times is greater than 400 and the time lag is between 50 and 150.

9. The method according to claim 2, characterized in that the correlation amplitude is calculated for different time lags and the time lag having the comparatively largest correlation amplitude is determined and used as the total amplitude.

10. The method according to claim 9, wherein the time lag with the comparatively largest total amplitude is associated with the fluorescent dye and stored in a database.

11. The method according to claim 2, wherein the correlation amplitude is calculated for different time lags and the mean value of the correlation amplitudes is determined and used as the total amplitude.

12. The method according to claim 2, wherein the correlation amplitude is calculated for different time lags and the sum of the correlation amplitudes is determined and used as the total amplitude.

13. The method according to claim 10, wherein the number of measuring times is greater than 400 and the time lag is between 50 and 150.

\* \* \* \* \*